US006007568A

United States Patent [19]

Harrell et al.

[11] Patent Number: 6,007,568

[45] Date of Patent: Dec. 28, 1999

[54] TRACTION TABLE

[76] Inventors: Eric A. Harrell, 570 #166 Bostwick Rd.; Robert H. Berry, 1102 E. Shore Dr., both of Ithaca, N.Y. 14850

[21] Appl. No.: 09/135,284

[22] Filed: Aug. 17, 1998

[51] Int. Cl.[6] ................................ A61F 5/00; A61H 1/02

[52] U.S. Cl. ............................ 606/242; 602/32; 602/19; 601/24; 482/907; 482/132; 482/142; 128/845

[58] Field of Search ................................ 602/18, 19, 32, 602/33, 38; 601/24, 26; 606/237, 240–243; 5/132, 613, 617, 621, 622, 624, 632, 633, 637, 640; 482/131, 132, 142, 907

[56] References Cited

U.S. PATENT DOCUMENTS

| | | | |
|---|---|---|---|
| 3,012,776 | 12/1961 | Hotas | 601/24 |
| 3,741,200 | 6/1973 | Morin | 606/243 |
| 3,771,518 | 11/1973 | Greissing | 606/243 |
| 3,913,155 | 10/1975 | Eary, Sr. | 5/632 |
| 4,243,025 | 1/1981 | Jones | 606/242 |
| 4,271,830 | 6/1981 | Moon | 5/613 |
| 4,649,905 | 3/1987 | Barnes | 606/245 |
| 5,176,706 | 1/1993 | Lee | 606/241 |
| 5,484,393 | 1/1996 | McCoy | 5/632 |

FOREIGN PATENT DOCUMENTS

| | | | |
|---|---|---|---|
| 1103159 | 10/1955 | France | 606/243 |
| 6-54870 | 3/1994 | Japan | 602/38 |

*Primary Examiner*—Richard J. Apley
*Assistant Examiner*—Victor K. Hwang
*Attorney, Agent, or Firm*—Brown, Pinnisi & Michaels, P.C.

[57] ABSTRACT

A table that corrects postures when looking at the anterior aspect of the person. The table will be mirror-imaging their postures including: Right and left head translations, right and left thoracic translations, and right and left lateral bending of the thorax. The table is made up of two movable sections (cervical and thoracic) and a stationary seat having a pelvic support. The head is placed in between two padded walls, and the cervical section is slid to one side and gets locked down, placing the head of the patient in the mirror-image translation. The thorax of the person is strapped down to the thoracic support, which is then slid to one side and locked in place, causing the thorax to be in mirror-image translation and/or lateral bending posture.

16 Claims, 2 Drawing Sheets

TRACTION TABLE

FIELD OF THE INVENTION

The invention pertains to the field of apparatus for treatment of patients. More particularly, the invention pertains to tables for treatment of spinal conditions by chiropractors and the like.

BACKGROUND OF THE INVENTION

It is well known that abnormal posture, such as translations, can lead to faulty mechanics of the spine. When left alone, these translations can result in migraine headaches and chronic low back pain syndromes, along with other head, neck, and low back ailments or symptoms. Furthermore, translations of the cervical and thoracic regions result in abnormal stresses of the neuromusculoskeletal system that over time can lead to irreversible degenerative changes.

Measurement of the translations present in the cervical and thoracic regions are routine diagnostic procedures. They include anterior to posterior cervical and thoracic x-rays. These x-rays must be, but not limited to in the case of physically impaired, taken in the erect position such that gravity plays a role along with weight bearing on the neuromusculoskeletal system.

SUMMARY OF THE INVENTION

This invention was developed to mirror image current postures of people, and take away the abnormal stresses present on the neuromusculoskeletal systems. Ultimately, this will alleviate the symptoms the person is experiencing and restore their posture. The invention comprises a table that corrects postures when looking at the anterior aspect of the person. The table will be mirror-imaging their postures including: Right and left head translations, right and left thoracic translations, and right and left lateral bending of the thorax. The table is made up of two moveable sections (cervical and thoracic) and a stationary seat or pelvic support. The head is placed in between two padded walls, and the cervical section is slid to one side and gets locked down, placing the head of the patient in the mirror-image translation. The thorax of the person is strapped down to the thoracic support, which is then slid to one side and locked in place, causing the thorax to be on a diagonal, to mirror-image the translation and/or lateral bending posture.

DESCRIPTION OF THE PREFERRED EMBODIMENT

Figure 3A:
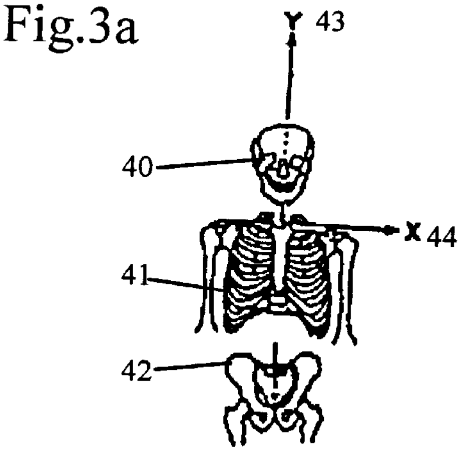
FIGS. 3*a* through 3*e* show diagrams of various spinal misalignments, and the mirroring applied by the invention.

This invention specifically relates to correcting postures of the cervical region in relation to the thorax and the thorax in relation to the pelvis. FIG. 3*a* shows a schematic of a patient, with cervical region (head/neck) (40), thorax (41) and pelvis (42) in alignment. All people will be viewed in the anterior to posterior direction prior to placement on the table in the supine position. When viewing the person, an x-ray of the cervical region (40), in relation to the thorax (41), in the anterior to posterior direction and of the thoracic region (41) in relation to the pelvis (42) in the anterior to posterior direction must be completed prior to placement on the table along the x-axis (44). The x-axis are defined as a real or imaginary line that runs left and right, about which coronal plane motion occurs. This view consists of visually reading the posture of the person from their feet to pelvis, the pelvis to the thorax, and thorax to the cervical region. The y-axis (43) is defined in these figures with relation to the pelvis (42).

Figure 3B:
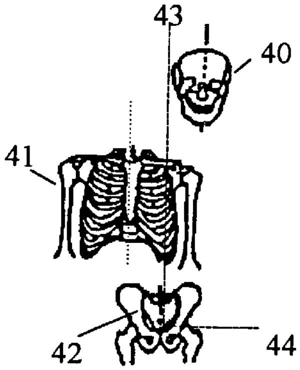

In FIG. 3*b*, the patient shows a thoracic translation and a head translation in opposite directions. That is, the patient's thorax (41) is offset to the right along the x-axis (44), and the head (40) is offset to the left. To correct this condition, the mirror-image placement of FIG. 3*c* is required.

Figure 3C:
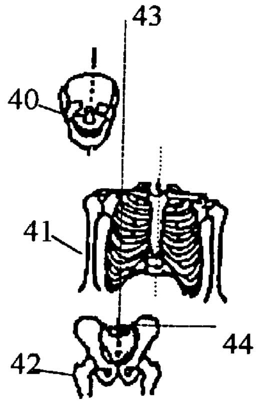
Figure 3D:
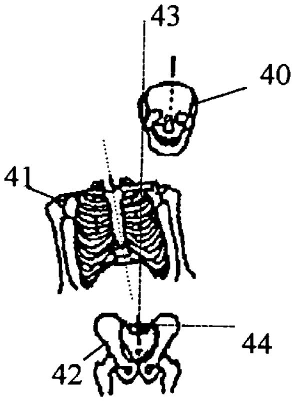

FIG. 3*d* shows a patient with a similar head (40) translation to the left as in FIG. 3*b*, but the thorax (41) is in a lateral bending posture to the right. In that case, the mirror-image placement of FIG. 3*e* would be desired.

Figure 3E:
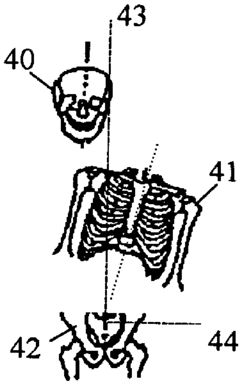

The table of the invention is designed to allow the practitioner, having diagnosed the misalignments exemplified by FIGS. 3*b* and 3*d*, to place and hold the patient in mirrored positions shown in FIGS. 3*c* and 3*e*.

Figure 1:
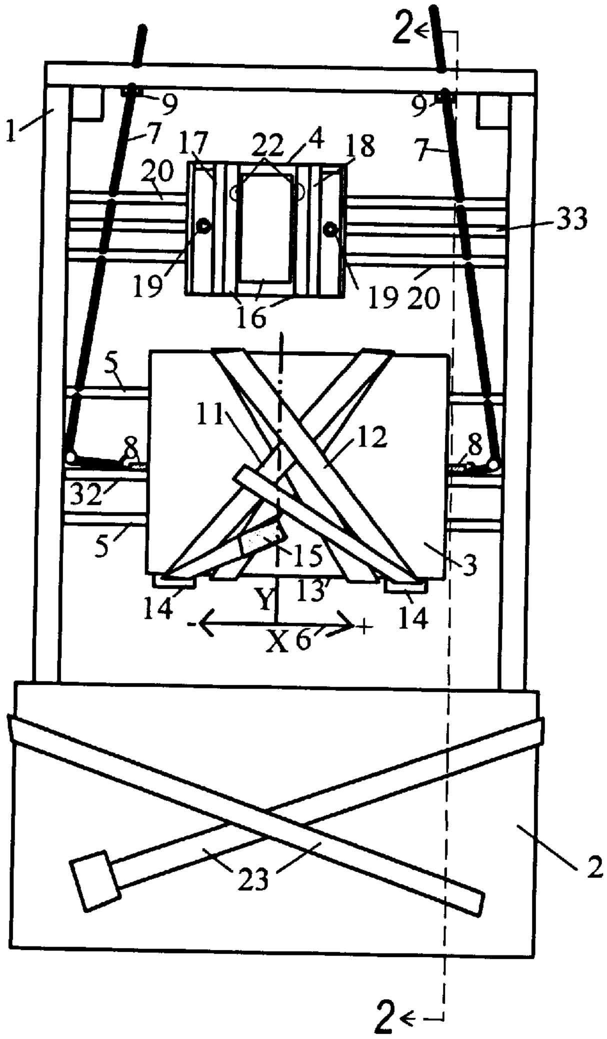
FIG. 1 shows a top view of the table of the invention.
Figure 2:
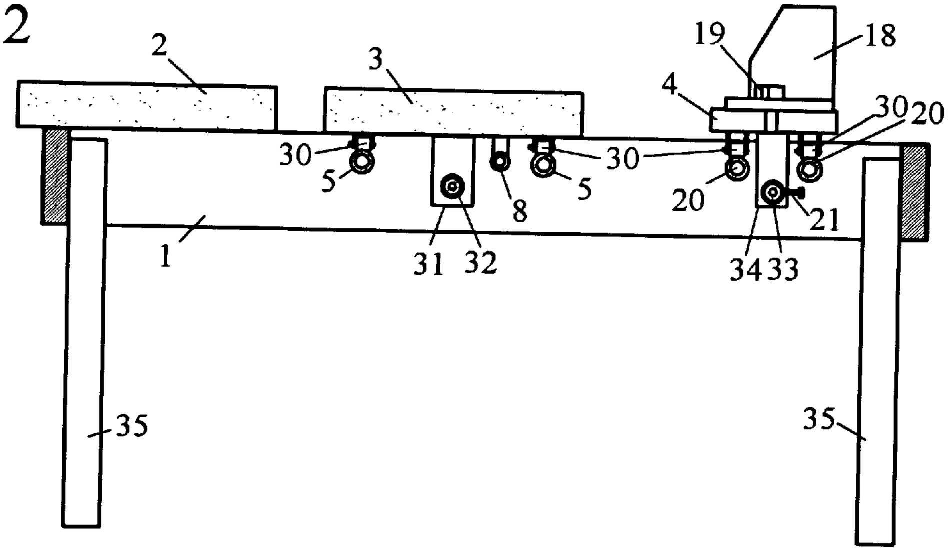
FIG. 2 shows a side view of the table of the invention, cut through lines 2—2 in FIG. 1.

FIGS. 1 and 2 show top and side views of the table of the invention. The table comprises a frame (1) mounted on legs (35), a stationary seat (2), a laterally movable thoracic support (3) for the torso and a movable cervical support (4) for the head. Straps (23) on the seat fasten across the patient's waist, holding the pelvic section in position on the seat (2).

The thoracic support (3) is supported by rails (5), on wheel assemblies (30) which ride on the rails (5), such that the thoracic support can be slid from side to side along the "x-axis" (6). A guide (31) surrounds a guide pipe (32), to constrain the forward and backward (x-axis rotation) motion of the thoracic support (3) as it rides from side to side (x-axis) on the rails (5). The motion of the thoracic support (3) is driven and constrained by, for example, lines (7) and springs (8). The lines (7) are routed under the table and exit at the head end through locks (9), so that the thoracic support (3) may be moved and locked in place by an operator viewing the patient longitudinally (along the "y-axis") as he or she lies on the table. The springs (8) produce a tension effect, allowing resistance against movement while not being entirely rigid. Alternatively, other methods of moving and holding the thoracic support in place could be used, such as worm gears, motorized, pneumatic or hydraulic actuators, etc.

The thoracic support (3) has straps (11)(12), which, when fastened, will cross the center of the patient lying supine on the table. One end of the straps (11)(12) is attached to the caudal (lower) side (13) of the thoracic support (3). The patient lies on the straps, and the straps are routed over the shoulders of the patient, crossing in the middle of the chest. They pass through loops (14), then back, to attach together with hook-and-loop fastening material (Velcro®) (15) or buckles or the like, in the middle of the chest region. This ensures that the patient has level shoulders and no lateral flexion of the spine is taking place.

The thoracic support (3) is preferably padded for the comfort of the patient, as by a foam pad which is preferably of 2" thick foam.

The cervical support (4) has padded (16) head pieces (17)(18), at least one of which can slide on the cervical support (4) to adjust to the width of the patient's head (preferably, both are adjustable, as shown), and then be clamped into place with clamps or locks (19). The padding (16) preferably includes ear holes (22) for comfort.

Similar to the thoracic support (3), the cervical support (4) is supported by wheels (30) on rails (20), such that it can be slid from side to side along the "x-axis" (6). A guide pipe (33) and guide (34) constrain rotational movement of the cervical support (4). A locking mechanism (21), such as a set-screw, cam or the like, locks the cervical support (4) into place on the guide pipe (33) or, if desired on rails (20). This locking mechanism (21) will hold the cervical support (4) in position, preventing movement of the head once the patient has reached mirror-image posture tolerance. This will allow precise translation of the head along the x-axis without inducing any coupling patterns of the spine.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A traction table comprising:

a) a frame having a head end and a lower end, first and second sides, and a y-axis running between the head end and the lower end equidistant between the first side and second side, and an x-axis perpendicular to the y-axis, extending between the first side and the second side;

b) a pelvic support mounted on the frame at the lower end thereof, comprising a surface for supporting the pelvis of a patient and a belt for holding the pelvis in place on the pelvic support;

c) a cervical support located proximate the head end of the frame, movably mounted to the frame for movement along a transverse path parallel to the x-axis, comprising a support platform, means for locking the cervical support in position relative to the y-axis, and a restraint for holding the head of the patient on the support platform;

d) a thoracic support located between the pelvic support and the cervical support, movably mounted to the frame for movement along a transverse path from the y-axis of the frame toward the first side or the second side, comprising a support platform, means for locking the thoracic support in position relative to the y-axis, and a restraint for holding the thorax of the patient on the support platform.

2. The traction table of claim 1, further comprising a plurality of rails transversely mounted to the frame underneath the cervical support, running from the first side to the second side, and means for supporting the cervical support upon the rails, mounted to the support platform and supported by the rails for motion thereon.

3. The traction table of claim 2, in which the means for supporting the cervical support are a plurality of wheels.

4. The traction table of claim 1, further comprising a plurality of rails transversely mounted to the frame underneath the thoracic support, running from the first side to the second side, and means for supporting the thoracic support upon the rails, mounted to the support platform and supported by the rails for motion thereon.

5. The traction table of claim 4, in which the means for supporting the cervical support are a plurality of wheels.

6. The traction table of claim 1, in which the restraint of the cervical support comprises first and second head restraint pieces mounted perpendicular to and extending above the support platform of the cervical support, such that the patient's head is placed between the first and second head pieces and restrained therebetween.

7. The traction table of claim 6, in which at least one of the first and second head pieces is slidably mounted to the support platform, such that the distance between the first and second head pieces may be varied to fit the patient's head.

8. The traction table of claim 6, further comprising pad means mounted to the first and second headpieces.

9. The traction table of claim 8, in which the pad means have ear holes for surrounding the patient's ears.

10. The traction table of claim 1, in which the restraint of the thoracic support comprises at least one strap for crossing the thorax of the patient, securing the thorax in place against the thoracic support.

11. The traction table of claim 1, further comprising a pad on the thoracic support.

12. The traction table of claim 1, further comprising means for laterally moving the thoracic support from the y-axis toward the first or second sides of the frame.

13. The traction table of claim 12, in which the means for moving the thoracic support comprise first and second lines running attached to the thoracic support and running at least to the first and second sides of the frame.

14. The traction table of claim 13 in which at least one of the first and second lines are attached to the thoracic support with a resilient member.

15. The traction table of claim 14 in which the resilient member is a spring.

16. The traction table of claim 14, further comprising means for locking at least one of the first and second lines to the frame of the traction table, such that the thoracic support may be locked in position.

* * * * *